United States Patent [19]
Hahn et al.

[11] Patent Number: 5,326,531
[45] Date of Patent: Jul. 5, 1994

[54] CO2 SENSOR USING A HYDROPHILIC POLYURETHANE MATRIX AND PROCESS FOR MANUFACTURING

[75] Inventors: Soonkap Hahn, Poway; Alan Nelson, San Diego; Monte Bennett, Escondido; Henry K. Hui, Laguna Niguel, all of Calif.

[73] Assignee: Puritan-Bennett Corporation, Carlsbad, Calif.

[21] Appl. No.: 989,102

[22] Filed: Dec. 11, 1992

[51] Int. Cl.$^5$ ...................... G01N 21/00; G01N 33/50
[52] U.S. Cl. ............................. 422/82.06; 422/82.03; 422/82.04; 422/82.07; 436/68; 385/123; 427/389.7; 427/407.2; 427/387
[58] Field of Search ............... 422/82.03, 82.04, 82.06, 422/82.07, 82.08, 82.09, 82.11; 436/68; 427/379, 389.7, 407.2, 387; 385/12, 122, 123

[56] References Cited

U.S. PATENT DOCUMENTS

| | | | |
|---|---|---|---|
| 31,879 | 5/1985 | Lübbers et al. | 436/133 |
| 3,114,610 | 12/1963 | Gafford et al. | 422/86 |
| 3,453,136 | 7/1969 | Bylsma | 427/407.2 |
| 3,754,867 | 8/1973 | Guenther | 422/91 |
| 3,904,373 | 9/1975 | Harper | 422/57 |
| 4,194,877 | 3/1980 | Peterson | 8/4 |
| 4,200,110 | 4/1980 | Peterson et al. | 128/634 |
| 4,321,057 | 3/1982 | Buckles | 4422/82.01 X |
| 4,399,099 | 8/1983 | Buckles | 422/58 |
| 4,456,542 | 6/1984 | Wagner et al. | 427/389.7 X |
| 4,468,229 | 8/1984 | Su | 8/507 |
| 4,476,870 | 10/1984 | Peterson et al. | 128/634 |
| 4,509,522 | 4/1985 | Manuccia et al. | 128/634 |
| 4,514,037 | 4/1985 | Bishop et al. | 427/407.2 X |
| 4,522,465 | 6/1985 | Bishop et al. | 427/407.2 X |
| 4,534,355 | 8/1985 | Potter | 204/403 |
| 4,548,907 | 10/1985 | Seitz et al. | 436/163 |
| 4,557,900 | 12/1985 | Heitzmann | 422/55 |
| 4,560,248 | 12/1985 | Cramp et al. | 350/96.34 |
| 4,568,518 | 2/1986 | Wolfbeis et al. | 422/56 |

(List continued on next page.)

FOREIGN PATENT DOCUMENTS

| | | | |
|---|---|---|---|
| 0105870 | 4/1984 | European Pat. Off. | 33/84 |
| 106086 | 5/1974 | Fed. Rep. of Germany | 21/52 |
| 2132348A | 7/1984 | United Kingdom | 35/52 |
| WO88/05533 | 7/1988 | World Int. Prop. O. | 21/00 |

OTHER PUBLICATIONS

Vurek, NTIS publ. 1983, PB83-189738 "Fiber-Optic Carbon Dioxide Partial Pressure Sensor".
G. G. Vurek et al., Ann. Biomed. Eng. 1983, 11, 499-510 "A Fiber Optic PCO$_2$ Sensor".
Z. Zhujun et al., Anal. Chim. Acta 1984, 160, 305-309 "A Carbon Dioxide Sensor Based on Fluorescence".

(List continued on next page.)

Primary Examiner—James C. Housel
Assistant Examiner—Milton I. Cano
Attorney, Agent, or Firm—Fulwider Patton Lee & Utecht

[57] ABSTRACT

The carbon dioxide sensor includes a CO$_2$ sensing matrix formed from a hydrophilic, gas permeable, cross-linked polyurethane. The polyurethane matrix is formed from a polyurethane pre-polymer mixture which cross links when mixed with an aqueous carbon dioxide buffer solution. The dye-buffer solution is physically entrapped as a homogeneous dispersion in the polymer matrix. The matrix is applied to the exposed glass core of an optical fiber, which may first be coated with a primer to allow the polyurethane matrix to bond firmly to the tip of the optical fiber. The hydrophilic polymeric matrix is preferably coated with a hydrophobic material to help avoid leaching of the dye from the matrix, and to prevent diffusion of hydronium ions into the sensing matrix. The hydrophobic polymer overcoat may thereafter be cured by heat treatment. The hydrophobic coating may also contain a light reflective material such as TiO$_2$.

16 Claims, 2 Drawing Sheets

U.S. PATENTS DOCUMENTS

| | | | |
|---|---|---|---|
| 4,587,101 | 5/1986 | Marsoner et al. | 422/56 |
| 4,608,344 | 8/1986 | Carter et al. | 422/82.11 |
| 4,657,736 | 4/1987 | Marsoner et al. | 422/56 |
| 4,712,865 | 12/1987 | Hsu et al. | 350/96 |
| 4,714,770 | 12/1987 | Hsu et al. | 556/419 |
| 4,737,343 | 4/1988 | Hirschfeld | 422/63 |
| 4,752,115 | 6/1988 | Murray, Jr. et al. | 350/96.29 |
| 4,798,738 | 1/1989 | Yafuso et al. | 427/2 |
| 4,816,130 | 3/1989 | Karakelle et al. | 422/82.03 |
| 4,824,789 | 4/1989 | Yafuso et al. | 436/68 |
| 4,830,924 | 5/1989 | Dallavia, Jr. | 427/389.7 X |
| 4,833,091 | 5/1989 | Leader et al. | 436/68 X |
| 4,842,783 | 6/1989 | Blaylock | 264/1.4 |
| 4,849,172 | 7/1989 | Yafuso et al. | 422/55 |
| 4,851,195 | 6/1989 | Matthews et al. | 436/68 X |
| 4,854,321 | 8/1989 | Boiarski | 128/634 |
| 4,867,919 | 9/1989 | Yafuso et al. | 264/1.5 |
| 4,886,338 | 12/1989 | Yasufo et al. | 422/55 X |
| 4,906,249 | 3/1990 | Fogt et al. | 8/647 |
| 4,919,891 | 4/1990 | Yasufo et al. | 436/68 |
| 4,921,589 | 5/1990 | Yates et al. | 204/157.5 |
| 4,925,268 | 5/1990 | Iyer et al. | 350/96.29 |
| 4,928,694 | 5/1990 | Maxwell | 128/637 |
| 4,934,369 | 6/1990 | Maxwell | 128/637 |
| 4,943,364 | 7/1990 | Koch et al. | 204/415 |
| 4,954,318 | 9/1990 | Yafuso et al. | 422/59 |
| 4,999,306 | 3/1991 | Yasufo et al. | 422/82.06 X |
| 5,047,208 | 9/1991 | Schweitzer et al. | 436/68 |
| 5,081,041 | 1/1992 | Yafuso et al. | 436/68 |
| 5,081,042 | 1/1992 | Yasufo et al. | 422/82.06 X |
| 5,098,659 | 3/1992 | Yim et al. | 422/82.06 X |
| 5,114,676 | 5/1992 | Leiner et al. | 422/82.06 |
| 5,120,510 | 6/1992 | Gourley et al. | 422/82.06 X |
| 5,139,601 | 8/1992 | Holmes-Farley et al. | 427/387 X |

OTHER PUBLICATIONS

W. W. Miller et al., Clin. Chem. 1987, 1538–1542 "Performance of an In–Vivo, Continuous Blood-Gas Monitor with Disposable Probe".

O. S. Wolfbeis et al., Anal. Chem. 1988, 60, 2028–2030 "Fiber-Optic Fluorosensor for Oxygen and Carbon Dioxide".

C. Munkholm et al., Talanta 1988, 109–112 "A Fiber-Optic Sensor for $CO_2$ Measurement".

S. J. Barker et al., Anesth Analg. 1989, 68, S1–S321 "Fiberoptic Intraarterial pHa, PaO2, and PaCO2 in the Operating Room".

H. K. Hui et al., SPIE vol. 1172 Chemical, Biochemical, and Environmental Sensors 1989, 1172, 233–237 "An Accurate, Low-Cost, Easily-Manufacturable Oxygen Sensor".

Kawabata et al., Anal. Chim. Acta, 1989, 219, 233 "Fiber-Optic Sensor for Carbon Dioxide with a pH Indicator Dispersed in a Poly (Ethylene Glycol) Membrane".

CO2 SENSOR USING A HYDROPHILIC POLYURETHANE MATRIX AND PROCESS FOR MANUFACTURING

BACKGROUND OF THE INVENTION

1. Field of the Invention

The present invention relates to carbon dioxide gas sensors used in automated chemical analysis and immunological testing. More particularly, the present invention relates to fiber optic sensors incorporating an improved carbon dioxide sensing element with a dye indicator in a polymer matrix suitable to be used in vivo in the body of a human or other animal.

2. Description of Related Art

The development and use of fiber optic sensors is a fast growing and competitive field. The first references to fiber optic sensors for detecting and quantitatively measuring gas concentrations emerged in the mid 1970's. Recent advances in fiber optic technology have increased the activity in the development and use of such sensors.

There is a strong interest in the medical field in developing in vivo sensors. Early efforts were applied in developing in vitro sensors and sensors for industrial uses. Many design criteria are important to the development of in vivo fiber optic sensor elements, requiring consideration of factors such as those related to the inability to control or prepare the sample, and the need to minimize the impact of the sensor's presence on the host organism. Fiber optic sensors must be biocompatible; the sensor must not adversely affect the host organism and the host organism must not adversely affect the sensor. The sensor must be small enough to be compatible with standard arterial devices, such as catheters. Moreover, the sensor must be engineered to be sterile, non-toxic, non-pyrogenic, and as blood compatible as possible.

Fiber optic sensors also must be economically integrable with conventional fiber optic apparatus. It is desirable that the fiber optic sensors be disposable and, therefore, economically inexpensive. Consequently, such sensors must be easy to manufacture, reproducible and simple to calibrate. Although other fiber optic sensors using polymers and indicating dyes have been proposed, many such sensors are too expensive to be considered disposable. Since the polymer chemistry of the sensor requires tedious and time-consuming manufacturing techniques, this also can make the sensors expensive and complex to manufacture, further limiting their use as a disposable.

Carbon dioxide fiber optic sensors are generally based on pH sensor technology. Such carbon dioxide sensors utilize hydrophilic polymers combined with pH fiber optic gas sensors to immobilize a hydrogen ion sensitive dye which is responsive to the carbon dioxide-bicarbonate equilibrium in an aqueous bicarbonate solution exposed to the dye. Semipermeable membranes are used to filter compromising artifacts and other analytes.

Conventional carbon dioxide sensors have incorporated reflectance, absorbance, and fluorescence dye indicators. Although reflectance indicators are well known, they are seldom used in pH or carbon dioxide sensors. A variety of polymeric materials have also been used to immobilize the carbon dioxide indicators for use in fiber optic sensors. When certain absorption indicators, such as phenol red, are in solution with polymers undergoing polymerization, such as acrylamide, the indicator becomes chemically bonded to the polymeric product. Covalent bonding with a polymeric substrate prevents the dye from being washed out of the polymer when exposed to an aqueous environment, such as blood. Covalently bonding the dye or indicator in a hydrophilic polymer substrate is often difficult to achieve and requires additional chemistries to obtain proper covalent bonds. Attempts to eliminate the chemical bonding requirement include creating micro-compartments within the polymer substrate. Covalently bonding a carbon dioxide dye indicator to a polymer and inclusion of a buffer system in the polymeric matrix have heretofore been a difficult, time consuming procedure. It would therefore be desirable to provide an alternative, effective and easy method of making a carbon dioxide sensor incorporating an indicator dye which will not wash out or leach out of the sensor.

Polymeric materials have also been used as a matrix for simply immobilizing fluorescent indicators. Such polymeric materials containing immobilized fluorescent dyes (for example, siloxane-based precursors and fluorescein derivatives) can be bonded to the distal end of optic fibers to provide a gas sensor. Since the indicators respond to any hydrogen ion artifact, such carbon dioxide sensors usually contain a carbon dioxide permeable, hydrophobic membrane. However, curing such hydrophobic membranes often created problems, since heat treatments to cure the polymeric dye indicator matrix can compromise the integrity of the sensor dye indicator material. Production methods known in the art can also create holes and other imperfections which may adversely affect the sensor. Moreover, the polymerization process and subsequent curing methods can often be expensive, cumbersome and unduly time extensive. Conventional fiber optic sensors incorporating polymers in a sensing matrix have used addition-type or condensation-type polymerization techniques to form the basic matrix material. Condensation and addition-type reactions require multiple monomers, catalysts and/or precursors to create the final form of the polymer. Moreover, such reactions are often time consuming, difficult to execute with precision, and are more expensive due to their multicomponent nature. Consequently, a need exists for a fiber optic $CO_2$ sensor that is easy to manufacture, has consistent geometry and chemistry, is easy to sterilize, is economically produced so that it can be disposable, and can reliably be used in vivo.

SUMMARY OF THE INVENTION

Briefly, and in general terms, the invention provides for an improved and useful sensor element for detecting carbon dioxide. The carbon dioxide sensor element of the invention is of a size capable of being attached to the distal end of a fiber optic filament. The filament and sensor are of a size to be used for in vivo use in human and other animal hosts. The sensor element is easy to manufacture and economical, allowing the sensor to be disposable.

The sensor element preferably comprises a hydrophilic, gas permeable, cross-linked polyurethane polymer which is formed from a liquid polyurethane prepolymer compound having a plurality of terminal isocyanate functional groups and which cross-links when mixed with an aqueous carbon dioxide dye-buffer solution to form a $CO_2$ sensing matrix. The dye-buffer solution is physically entrapped in the polymer matrix, and the hydrophilic polymeric matrix is preferably coated with a hydrophobic polymer to help avoid leaching of the dye from the matrix, and to prevent diffusion of hydronium ions to the sensing matrix.

The cross-linking of the polyurethane matrix is preferably initiated at room temperature by the addition of the aqueous dye-buffer solution to the liquid polyurethane prepolymer mixture, rather than by application of heat, which helps to preserve the integrity of the dye indicator material. Thus, the reaction can be carried out in a short time span at room temperature. The use of a hydrophilic polymer which cross-links to entrap a dye-buffer solution in the present invention eliminates the need for multiple precursors or other monomers in the reaction. This method produces a dye-polymer matrix having excellent mechanical strength characteristics. The optical fiber may also be advantageously coated with a primer to allow the polyurethane matrix to bond firmly to the tip of the optical fiber.

In a preferred embodiment of the invention, 15 the polymeric material is formed from polyurethane, and the dye is a fluorescent pH indicator, such as 8-hydroxy-1,3,6-pyrenetrisulfonic acid (HPTS). The aqueous buffer is preferably a physiological pH range bicarbonate buffer solution. When the uncured pre-polyurethane is mixed with the aqueous dye-buffer solution, the dye-buffer solution forms a dispersion in the matrix. As the polyurethane cross-links, the dye-buffer solution dispersion is thus physically entrapped within the polymeric matrix. The carbon dioxide sensing element can thus be formed by dipping the distal end of a fiber optic core into the matrix before the matrix is completely cured, and the matrix is then allowed to cure on the fiber at room temperature.

The cured sensing matrix is then preferably coated with a hydrophobic, gas permeable polymeric material such as silicone. The hydrophobic coating also preferably contains a light reflective material such as $TiO_2$. The fiber optic filament containing the polymeric matrix can be coated by simply dipping the distal end of the fiber into the hydrophobic polymeric material. The hydrophobic polymer overcoat may thereafter be cured by heat treatment.

A fiber optic carbon dioxide sensor may thus be manufactured easily and economically using the method of the invention, which provides a $CO_2$ sensor within a hydrophilic, ion impermeable, gas and light permeable polymer which cross-links upon mixture with an aqueous dye-buffer. While the $CO_2$ chemistry is polymerized, the aqueous dye-buffer is physically entrapped into the polymer matrix. To prevent depletion of the physically entrapped dye upon hydration of the sensor, the chemistry part is overcoated with a gas permeable hydrophobic polymer such as silicone.

Other features and advantages of the present invention will become apparent from the following detailed description, taken in conjunction with the accompanying drawings, which illustrate, by way of example, the principles of the invention.

DESCRIPTION OF THE PREFERRED EMBODIMENTS

Figure 1:
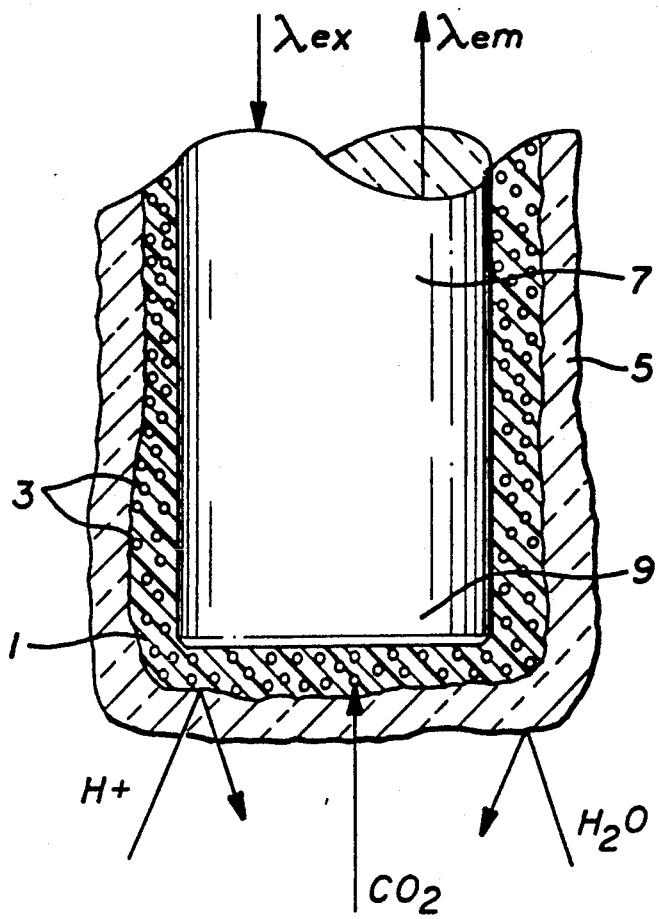
FIG. 1 is a schematic representation illustrating the operation of the carbon dioxide sensor of the invention.

Heretofore, sensors for carbon dioxide detection were often unsuitable for in vivo use. Conventional blood gas sensors exhibited a tendency to leach out the dye indicator materials incorporated in the sensor. In order to overcome this problem, various complex methods of covalently bonding the dye indicator materials and compartmentalizing the sensor element have been devised. However, such carbon dioxide sensing elements were often cost prohibitive for use with disposable fiber optic sensors, and were often difficult to manufacture.

As shown in the drawings, which are provide to illustrate by way of example, the present invention is embodied in a fiber optic carbon dioxide gas sensor which is easy and inexpensive to manufacture, and which entraps the dye indicator material to prevent leaching of the dye indicator material from the sensor during in vivo use.

Referring to the drawings, and more particularly to FIG. 1, in a preferred embodiment of the carbon dioxide ($CO_2$) sensor element of the invention, an end portion of the sensor is shown in exemplary configuration to illustrate the basic principles of operation of the sensor. The $CO_2$ sensing element of the sensor includes a matrix 1 formed from a hydrophilic, gas permeable polymer, containing a homogeneous dispersion of an aqueous $CO_2$ dye-buffer solution 3. The polymeric matrix is preferably a cross-linked polyurethane formed from a liquid polyurethane pre-polymer compound having a plurality of terminal isocyanate functional groups, in which a cross-linking reaction is initiated upon mixture with the aqueous dye-buffer solution. Polyurethane is particularly advantageous for this use because of its gas permeable nature, which allows for a rapid diffusion of carbon dioxide to the dye indicator material in the sensing matrix. By mixing and curing the mixture at room temperature, the dye-buffer solution 3 is physically entrapped within the hydrophilic $CO_2$ sensing matrix 1.

The buffer solution preferably includes bicarbonate, and the dye included in the dye-buffer solution is preferably one which is sensitive to changes in pH, such as HPTS and the like, so that isolation of the sensing element from direct exposure to pH changes, and diffusion of $CO_2$ into the sensing element from the sample to be monitored to affect the pH within the dye-buffer solution in the sensor make the dye responsive to $CO_2$ levels in the sample.

To prevent depletion of the dye-buffer solution 3 by leaching into the sample, the $CO_2$ sensing matrix is preferably also coated with a hydrophobic, gas permeable material 5, such as silicone, which also preferably contains a reflective material such as $TiO_2$. Both the hydrophilic polymer matrix 1, and hydrophobic coating 5 surround the exposed distal end of the fiber optic core 7.

As is illustrated in FIG. 1, the exterior semipermeable hydrophobic coating of the sensor prevents water, hydronium ions and other ions and various blood constituents which might otherwise interfere with the sensor from entering the hydrophilic sensing matrix, while allowing $CO_2$ to diffuse into the sensing matrix. Carbon dioxide diffuses through the hydrophobic membrane and the hydrophilic sensing matrix into the aqueous solution, affecting the following well known equilibrium:

$$CO_2 + H_2O \rightleftharpoons H_2CO_3H^+ + HCO_3^-$$

$CO_2$ will pass through the polymeric membrane, as it is gas permeable. However, hydrogen ions from the environment will not pass through the polyurethane polymeric matrix, as it is covered with the layer of hydrophobic material, which is substantially ion impermeable. Since both the hydrophobic coating and the polymer matrix are gas permeable, diffusion of carbon dioxide to the dye indicator material is rapid, which allows for fast response times of the gas sensor.

Figure 2:
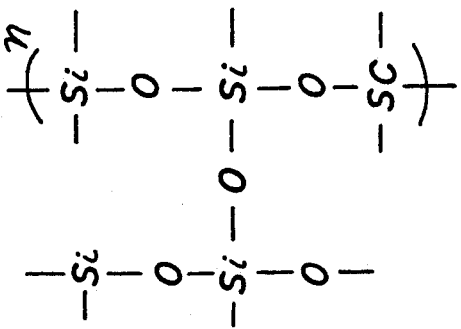
FIG. 2 illustrates the cross-linking reaction of the pre-polymer material which occurs in the presence of the aqueous dye-buffer solution, and the bonding of the cross-linked polymeric matrix to the glass surface of an optical fiber.
Figure 2:
Figure 2:
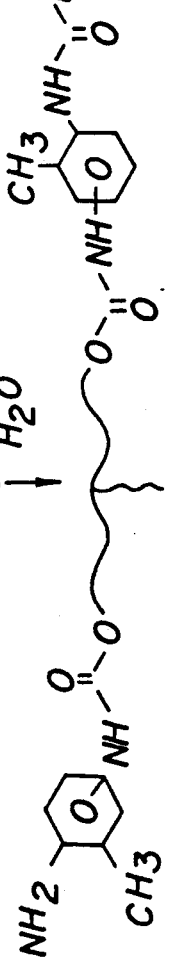
Figure 2:
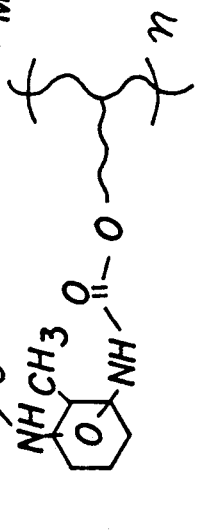

The fluorescent dye indicator in the dye-buffer solution dispersed throughout the sensing matrix emits a characteristic wavelength of light ($\lambda em$) when irradiated by an excitation wavelength of light ($\lambda ex$). The intensity of the emission wavelength of such dye indicators is used to indicate hydrogen ion concentration, since the emission wavelength intensity is a function of chemical changes of the fluorescent indicator due to hydrogen ion effects. Many fluorescent indicators suitable for carbon dioxide concentration detection are known. Such indicators include betamethylumbelliferone, fluorescein, and HPTS. HPTS is preferred due to its relative photostability, ability to be ratioed, and low toxicity in mammals. As can be seen in FIG. 2, the gas permeable, hydrophilic polymeric matrix is preferably formed from a polyurethane pre-polymer, preferably having a plurality of terminal isocyanate functional groups, such as polyether polyisocyanate, available from W. R. Grace under the trade name HYPOL 2002. The polyurethane pre-polymer will cross-link in the presence of water, and polymerizes when mixed with the aqueous dye-buffer solution, forming a homogeneous dispersion of the dye-buffer solution in the matrix. The cross-linking polyurethane polymer also bonds to the exposed glass surface of the fiber core. The resulting polyurethane matrix physically entraps the aqueous dye-buffer within the matrix. A simple mixing procedure of the polyurethane precursor and the dye-buffer solution insures substantially uniform dispersion of the dye-buffer within the polymer matrix.

In the method of manufacturing the sensor of the invention, the hydrophilic polymer matrix and the physically entrapped, $CO_2$ indicator dye-buffer solution are currently typically prepared by a simple mixing process. An aqueous buffer solution is prepared by mixing sodium bicarbonate and sodium chloride in water. The concentration of bicarbonate is preferably determined so as to yield optimum sensitivity in a physiologically useful range of carbon dioxide blood levels. The concentration of sodium chloride is preferably determined so as to be generally isotonic with blood for intravascular use.

The sensing matrix 1 may be easily fixed to the light conductive core of the fiber optic filament 7. Upon mixing, the hydrophilic pre-polymer and aqueous dye-buffer solution form a viscous matrix. The carbon dioxide sensor can be manufactured by first stripping a small section of the cladding from the distal end of the fiber. Commercially available fiber optic cores and cladding material may be used. The exposed glass surface of the distal end 9 of the optical fiber 7 may advantageously coated with a priming compound, such as 3-isocyanatopropyltriethoxysilane or the like, to enhance firm bonding between chemistry parts and fiber and for improved mechanical strength of the sensor. The priming compound is preferably applied just before the distal end 9 is coated with the hydrophilic polymer matrix 1. The stripped portion of the filament's distal end 9 is preferably coated with the hydrophilic polymer matrix 1 by a dipping process before the matrix cures. Since the polyurethane pre-polymer cross-links and polymerizes at room temperature rapidly upon addition to the dye-buffer, the distal end 9 of the fiber optic filament is preferably dipped immediately into the resulting polymeric matrix, and the homogeneous dispersion of the dye-buffer solution 3 is physically entrapped in the matrix as the matrix cures. The resulting $CO_2$ sensor may then be protected from depletion of the aqueous dye buffer by dipping the polymeric matrix and distal end of the filament into a solution of a hydrophobic, gas permeable polymeric substrate such as silicone. The coating is typically cured at about 100° C. for a period of about one-half hour.

This room temperature cross-linking reaction of the polymeric matrix which occurs upon mixing with the aqueous dye-buffer solution alleviates the need for thermal curing or complex chemistry bonding methods. A typical cure time for the polyurethane mixture is about five minutes at room temperature, thus protecting the sensor from potentially damaging temperatures often required in the curing of other polymers.

Figure 3:
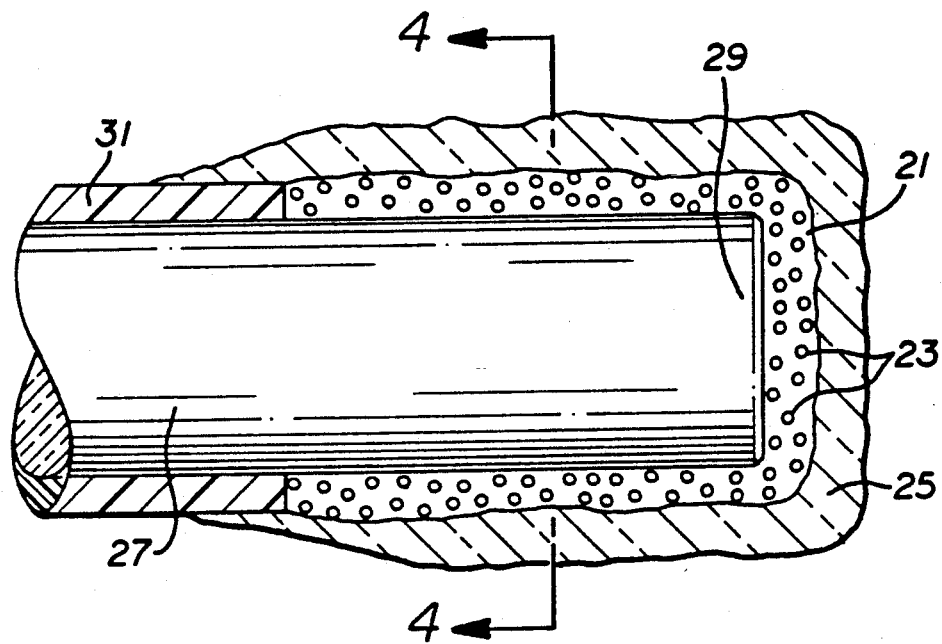
FIG. 3 is a longitudinal cross-section of the carbon dioxide gas sensor of the present invention.

As is shown in FIG. 3, which illustrates the distal portion of a preferred embodiment of the sensor of the invention, the hydrophobic polymer coating 25 is also preferably applied to the outer surface of the hydrophilic matrix so as to overlap with the fiber optic cladding 31. This outer coating of hydrophobic material 25 also preferably contains a light reflective material such as titanium dioxide, so as to retain the excitation and emission wavelengths of light and to protect the sensing element from comprising light artifacts. Other light reflective materials, such as ferrous oxide, may also be suitable for use in the hydrophobic, gas permeable, reflective polymer coating.

The hydrophilic polymer matrix 21 may be formed from a hydrophilic polyurethane pre-polymer such as polyether polyisocyanate, which may be obtained under the trade name of HYPOL 2002 from W.R. Grace. The dye component of the aqueous dye-buffer solution 23 is preferably HPTS (1-hydroxy-3,6,8-pyrenetrisulfonate), in a sodium bicarbonate buffer. A standard optic filament 27, having a typical diameter of about 125 microns, may also have a cladding 31 formed from a protective material such as Teflon. The distal end 29 is preferably dipped in the active viscous material which results from cross-linking of the polyurethane pre-polymer with the aqueous dye-buffer solution 23. The matrix 21 is typically cured in situ on the distal end 29 at room temperature, after about five minutes.

Figure 4:
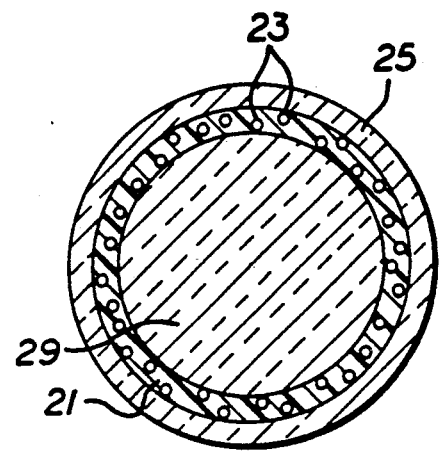
FIG. 4 is a cross-sectional view of the carbon dioxide sensor taken along line 4—4 of FIG. 3.

Further referring to FIG. 3, the fiber and sensing matrix is coated with a light reflective hydrophobic polymer 25. The hydrophobic polymer coating 25 prevents depletion of the physically entrapped dye-buffer solution 23 upon hydration of the sensor. The hydrophobic coating 25 prevents ions from passing into the sensing element, and prevents the aqueous dye-buffer solution from leaching out of the sensor. The coating 25 is preferably formed of silicone mixed with titanium oxide. The hydrophilic polymer matrix 21 and hydrophobic polymer coating 25 generally completely surround the fiber core's distal end 29, as is shown in FIG. 4. The aqueous dye-buffer solution 23 should be substantially uniformly dispersed along the outside perimeter of the distal end 29. The thickness of the matrix 21 and coating 23 should not unduly increase the overall diameter of the sensor.

EXAMPLE 1

To prepare the hydrophilic sensor matrix, prepare a 40% mixture of a hydrophilic polyurethane pre-polymer (polyether polyisocyanate, HYPOL 2002-W.R. Grace) and dimethylformamide (DMF). Five parts of the 40% HYPOL 2002 and DMF mixture is mixed manually with one part of aqueous dye-buffer solution, which is a mixture of 7mM of HPTS, 35mM of sodium carbonate and 10mM sodium chloride. The mixture starts thickening and cross-linking as the pre-polymer is mixed with the aqueous solution. The dye-buffer solution and polymerizing polyurethane should be mixed to a substantially uniform matrix to form a homogeneous dispersion of the dye-buffer solution in the matrix. The distal end of a fiber optic element is primed by treatment with 3-isocyanatopropyltriethoxysilane. The fiber optic core's distal end is then dipped into the viscous material or applied to the distal end. The fiber and matrix sensor is then allowed to cure for five minutes at room temperature.

EXAMPLE 2

The hydrophilic sensor matrix is prepared as in Example 1, and a hydrophobic silicone overcoat is prepared by mixing two grams of polysiloxane PSP051 (Petrarch, Inc.), 50% $TiO_2$, 0.2 grams of polysiloxane PS 122.5 (Petrarch, Inc.), and two drops of 100% PCO 72 in hexane. The fiber optic core with cured hydrophilic matrix is dipped into the silicone mixture. This overcoating is cured in an oven at 100° C. for 20 minutes. After curing, the sensors are stored in saline.

It should be recognized that while the cross-linking of the polymer matrix is preferably carried out at room temperature, avoiding damage to the chemistry from heating, it may be possible to accelerate the curing process with the application of mild heat without substantially degrading the dye indicator material.

It can thus be seen that the invention provides for a new, improved sensor element and protective coating which may be used with conventional fiber optic systems. The sensor is compatible with the fiber optics to allow in vivo use with standard gauge catheters. Likewise, the sensor has in vitro uses for analytical measurements. The simple mixing process is advantageous over previously used addition and condensation polymerization reactions. The sensing element is reliable and economical, and therefore suitable for use in disposable fiber optic sensors.

While a particular form of the invention has been illustrated and described, it will be apparent that various modifications can be made without departing from the spirit and scope of the invention. Accordingly, it is not intended that the invention be limited, except as by the appended claims.

What is claimed is:

1. A carbon dioxide sensor element comprising:
   an optical fiber having a surface portion;
   a hydrophilic, gas permeable, cross-linked polymeric matrix disposed over std optical fiber surface portion, said hydrophilic polymeric matrix containing an aqueous dye-buffer solution physically entrapped in and dispersed throughout said hydrophilic polymeric matrix, said hydrophilic polymeric matrix formed from a polyurethane pre-polymer compound having a plurality of terminal isocyanate functional groups, said polyurethane pre-polymer compound being cross-linked by addition of said aqueous dye-buffer solution at room temperature; and
   a layer of a gas permeable, hydrophobic material coating said hydrophilic polymeric matrix.

2. The carbon dioxide sensor element of claim 1, wherein the aqueous dye-buffer solution includes a fluorescent dye in a bicarbonate buffer.

3. The carbon dioxide sensor element of claim 2, wherein said fluorescent dye is hydroxypyrenetrisulfonic acid or a derivative thereof.

4. The carbon dioxide sensor element of claim 1, wherein said hydrophobic layer of material includes a reflective material.

5. The carbon dioxide sensing element of claim 4, wherein said reflective material comprises titanium dioxide.

6. The carbon dioxide sensing element of claim 1, wherein said hydrophobic material is silicone.

7. A method of manufacturing a carbon dioxide sensor element including an optical fiber having a surface portion covered with a hydrophilic, gas permeable, cross-linked polymeric matrix containing a homogeneous dispersion of an aqueous dye-buffer solution physically entrapped in said hydrophilic polymeric matrix, and a layer of a gas permeable, hydrophobic material coating said hydrophilic polymeric matrix, comprising the steps of:
   mixing a hydrophilic, semipermeable, pre-polymer material which cross-links in the presence of water with an aqueous dye-buffer solution, to form a homogeneous dispersion of said dye-buffer solution in said pre-polymer material and initiate cross-linking of said pre-polymer material;
   applying said pre-polymer material in which cross-linking has been initiated to said surface portion of said optical fiber;
   curing said pre-polymer material in which cross-linking has been initiated at room temperature, to form said hydrophilic, polymeric matrix on said optical fiber, and to thereby physically entrap said aqueous dye-buffer solution in said polymeric matrix; and
   coating said hydrophilic polymeric matrix with a layer of hydrophobic, gas permeable material.

8. The method of claim 7, wherein said pre-polymer comprises polyether polyisocyanate.

9. The method of claim 7, wherein said optical fiber has distal and proximal ends, and a glass core covered with a cladding material, and further comprising the step of:
   removing said cladding material from said core at said distal end of the optical fiber prior to said step of applying said pre-polymer material in which cross-linking has been initiated.

10. The method of claim 9, further comprising the step of coating the distal end of said optical fiber from which said cladding has been removed with a priming compound before applying said pre-polymer material in which cross-linking has been initiated.

11. The method of claim 10, wherein said priming compound comprises 3-isocyanatopropyltriethoxysilane.

12. A method of manufacturing a carbon dioxide sensor element including an optical fiber having a surface portion covered with a hydrophilic, gas permeable, cross-linked polymeric matrix containing a homogeneous dispersion of an aqueous dye-buffer solution physically entrapped in said matrix, and a layer of a gas permeable, hydrophobic material coating said hydrophilic matrix, comprising the steps of:

mixing an aqueous dye-buffer solution with a hydrophilic, semipermeable, polyurethane pre-polymer material having a plurality of terminal isocyanate functional groups, to form a homogeneous dispersion of said dye-buffer solution in said polyurethane pre-polymer material and to initiate cross-linking of said polyurethane pre-polymer material to entrap said dye-buffer solution in said polyurethane pre-polymer material;

applying said polyurethane pre-polymer material in which cross-linking has been initiated to said surface portion of said optical fiber;

curing said polyurethane pre-polymer material in which cross-linking has been initiated at room temperature, to form said hydrophilic, polymeric matrix on said optical fiber, and to thereby physically entrap said aqueous dye-buffer solution in said polymeric matrix; and coating said hydrophilic polymeric matrix with a layer of hydrophobic, gas permeable material.

13. The method of claim 12, wherein said polyurethane pre-polymer material comprises polyether polyisocyanate.

14. The method of claim 12, wherein said optical fiber has distal and proximal ends, and a glass core covered with a cladding material, and further comprising the step of:

removing said cladding material from said core at said distal end of the optical fiber prior to said step of applying said polyurethane pre-polymer material in which cross-linking has been initiated.

15. The method of claim 14 further comprising the step of coating the distal end of said optical fiber from which said cladding has been removed with a priming compound before applying said polyurethane pre-polymer material in which cross-linking has been initiated.

16. The method of claim 15, wherein said priming compound comprises 3-isocyanatopropyltriethoxysilane.

* * * * *

UNITED STATES PATENT AND TRADEMARK OFFICE
CERTIFICATE OF CORRECTION

PATENT NO. : 5,326,531
DATED : July 5, 1994
INVENTOR(S) : Soonkap Hahn, Alan Nelson, Monte Bennett, Henry K. Hui It is certified that error appears in the above-indentified patent and that said Letters Patent is hereby corrected as shown below:

In Column 3, line 20, delete "15";

In Column 5, line 7, delete equation, insert --$CO_2 + H_2O \leftrightarrows H_2CO_3 \rightleftarrows H^+ + HCO_3^-$ --;

In Column 7, line 67, delete "std", insert --said--.

Signed and Sealed this

Twenty-second Day of November, 1994

Attest:

BRUCE LEHMAN

*Attesting Officer*     *Commissioner of Patents and Trademarks*